US006603026B2

United States Patent
Lightner

(12) 
(10) Patent No.: US 6,603,026 B2
(45) Date of Patent: Aug. 5, 2003

(54) HETEROCYCLIC COMPOUNDS PRODUCED FROM BIOMASS

(76) Inventor: Gene E. Lightner, 706 SW. 296th St., Federal Way, WA (US) 98023

( * ) Notice: Subject to any disclaimer, the term of this patent is extended or adjusted under 35 U.S.C. 154(b) by 99 days.

(21) Appl. No.: 09/923,644

(22) Filed: Aug. 7, 2001

(65) Prior Publication Data

US 2003/0032819 A1 Feb. 13, 2003

(51) Int. Cl.$^7$ .................... C07D 307/46; C07D 307/50; C07D 307/48
(52) U.S. Cl. ................. 549/488; 549/489; 549/490
(58) Field of Search ............................... 549/488, 489, 549/490

(56) References Cited

U.S. PATENT DOCUMENTS

| 2,559,607 | A | * | 7/1951 | Dunning et al. | ............ 549/490 |
| 2,779,770 | A | * | 1/1957 | Cass | ........................ 549/490 |
| 4,612,286 | A | | 9/1986 | Sherman et al. | ............ 435/157 |
| 4,740,605 | A | | 4/1988 | Rapp | .......................... 549/483 |

OTHER PUBLICATIONS

Wise, Bioconversion Systems, CRC Press, Boca Raton, Florida, pp. 90–92 (1984).*
Wise, Liquid Fuel Systems, CRC Press, Boca Raton, Fl., p. 2–7, 88–95 and 155–157 (1983).*
Organic Chemistry 1943 Hill and Kelly pp. 780–781 p. 778.
ACS Meeting 28 Aug. 2, 1983 Wright p. 2.
Handbook of Chemistry And Physics. 56$^{th}$ Edition 1975–1976 Edited by R.C. Weast p. D–14.
56$^{th}$ Edition
Merck index Eighth edition 1968 Edited by P.G. Stecher p. 552.
Chemical Process Industries, 2$^{nd}$ edition 1956 Shreve p. 840.
Publicion on the internet 2001 Larrson, et al. p. 1.

* cited by examiner

Primary Examiner—Bernard Dentz

(57) ABSTRACT

Sugars derived from acidic hydrolysis of biomass consist of glucose and xyloses which are subjected to dehydration, within the hydrolysis environment, to form heterocyclic compounds, furfural and hydroxymethylfurfural. By providing a vessel for hydrolysis of biomass, a hydrolysate containing acid and heterocyclic compounds is formed. Upon withdrawing the hydrolysate from the vessel, and employment of separating means for removing heterocyclic compounds from the hydrolysate, a hydrolysate substantially devoid of heterocyclic compounds is provided for recycle to the vessel and will provide heterocyclic compounds. By withdrawing solids, containing lignins remaining from hydrolysis of biomass, from the vessel, and filtering the solids, to result in a filtrate for recycle to the vessel and provide filtered solids for subsequent processing. Thereby, heterocyclic compounds are derived from a biomass and withdrawn from the hydrolysis vessel, and solids, remaining from hydrolysis of biomass, are withdrawn from the hydrolysis vessel.

20 Claims, 2 Drawing Sheets

HETEROCYCLIC COMPOUNDS PRODUCED FROM BIOMASS

BACKGROUND OF THE INVENTION

Present day interest in hydrolysis of biomass is to provide an alternative fuel source to avoid dependence on unreliable imported petroleum crude oil for liquid fuels. Characteristic dry biomass composition is: lignin 25%, hemicellulose 25%, amorphous cellulose 10%, and crystalline cellulose 40%. Biomass is selected from the group consisting of wood, waste paper and municipal solid waste including an individual or a combination thereof.

Acid for hydrolysis is selected from the group consisting of inorganic acids and organic acids including sulfuric acid.

Furfural is produced by hydrolysis of hemicellulose to produce pentose sugars subjected to dehydration to form furfural. Furfural is undesired in a hydrolysate for fermentation because furfural of sufficient concentration in the hydrolysate will substantially inhibit growth of microorganisms required for fermentation, professed by Sherman, et al., in U.S. Pat. No. 4,612,268.

A hydrolysate containing hydroxymethylfurfural derived from dehydration of glucose formed by hydrolysis of a biomass, decreases contents of glucose for fermentation. The unwanted effect of hydroxymethylfurfural and furfural, within the hydrolyzate, in providing inhibition of fermentation to produce ethanol within fermentation is contributed by Larsson, et al., on the internet, entitled "The generation of fermentation inhibitors during dilute acid hydrolysis of softwood".

A state of the art process "process for preparing pure 5-hydroxymethylfuraldehyde" is described by Rapp, in U.S. Pat. No. 4,740,605, wherein saccharides are acid catalyzed to form HMF followed by extraction and chromatography to purify HMF.

It is therefore an object of this invention to obviate many of the limitations or disadvantages of the prior art.

The present concern is about producing heterocyclic compounds from a biomass.

A distinct object of this invention is to provide liquid fuels from a biomass without depending on fermentation.

Still another object of this invention is to provide heterocyclic compounds derived from acidic hydrolysis of a biomass.

Yet another object of this invention is to withdraw solids, containing lignins, from a biomass.

With the above and other objects in view, this invention relates to the novel features and alternatives and combinations presently described in the brief description of the invention.

APPLICATIONS AND BACKGROUND OF THE INVENTION

Heterocyclic compounds such as furfural and hydroxymethylfurfural are derived from acidic hydrolysis of biomass. Heterocyclic compounds having five rings of four carbon atoms and one oxygen atom consisting of furfural and hydroxymethylfurfural are described in Organic Chemistry, 1948, authored by Hill and Kelley, page 778 and pages 780–781 Acidic hydrolysis of biomass, containing hemicellulose and cellulose, form xyloses and glucose which are respectively subjected to dehydration, within the hydrolysis environment, to form heterocyclic compounds, furfural and hydroxymethylfurfural.

Hydrolysis of lignocellulose (biomass) kinetics for formation of hydroxymethylfurfural and furfural is described in "High temperature acid hydrolysis of cellulose for alcohol fuel production" by John D. Wright, prepared under task No. 3491 by the solar research institute, Golden Colo., for publication by the American Chemical Society Meeting, Aug. 28 to Sep. 2, 1983, page 2. Hydroxymethylfurfural and furfural, within a hydrolyzate, are undesirable compounds accompanying sugars and must be separated prior to fermentation, so stated.

Solvents to dissolve hydroxymethylfurfural and furfural are disclosed in the Merck index, eighth edition, 1968, page 552. Organic solvents capable of dissolving heterocyclic compounds referred to include ether, benzene and chloroform. A solvent capable of dissolving heterocyclic compounds and insoluble in aqueous solutions is selected from the group consisting of organic solvents and cyclic compounds including an individual or a combination thereof If chloroform, for example, is employed as a solvent for extraction, a hydrolysate containing the solvent or a solution containing the solvent and hydroxymethylfurfural and furfural is formed. Distillation likely forms an azeotrope which can then utilized to recover solvent from the ensuing azeotrope, by condensation of two layers and separation of the layer rich in solvent and subjecting the layer poor in solvent to distillation. Formation of a binary chloroform and water azeotrope is disclosed in the Handbook of Chemistry and Physics, 56th edition, 1975–1976, page D-14.

An example of using furfural as a solvent is described on page 840, in Chemical Process Industries, second edition, authored by R. N. Shreve, in which furfural is employed to dissolve lube oil to produce a solution for subsequent separation.

BRIEF DESCRIPTION OF THE INVENTION

The present invention, in its broadest aspect, comprises a method to form heterocyclic compounds from a biomass which constitutes providing a vessel for hydrolysis, and providing a biomass to the vessel. Thereupon subjecting biomass to hydrolysis within the vessel, to form glucose and xyloses which are subjected to dehydration, within the hydrolysis environment, to form heterocyclic compounds, furfural and hydroxymethylfurfural within a hydrolysate, containing acid and heterocyclic compounds. Hydrolysate, formed by hydrolysis, is withdrawn from the vessel, and subjected to separating means for dividing heterocyclic compounds to provide a hydrolysate substantially devoid of heterocyclic compounds for recycle. Solids, remaining from hydrolysis of biomass, is removed from the vessel. The removed solids are subjected to filtering resulting in a filtrate of a hydrolysate for recycle and filtered solids, remaining from hydrolysis of biomass, subjected to subsequent processing.

Characteristics of the invention include,

Sugars obtained by hydrolysis are susceptible to dehydration to form hydroxymethylfurfural and furfural.

Heterocyclic compounds are derived from a biomass by hydrolysis within a vessel.

Hydrolysate, formed by hydrolysis, is withdrawn from the vessel,

Solids, remaining from hydrolysis of biomass, containing lignins, is removed from the vessel The method is customarily accomplished in a continuous fashion.

BRIEF DESCRIPTION OF THE DRAWINGS

The features that are considered characteristic of this invention are set forth in the appended claims. This invention, however, both as to its origination and method of operations as well as additional advantages will best be understood from the following description when read in conjunction with the accompanying drawings in which:

DETAILED DESCRIPTION OF THE PREFERRED EMBODIMENT

Figure 1:
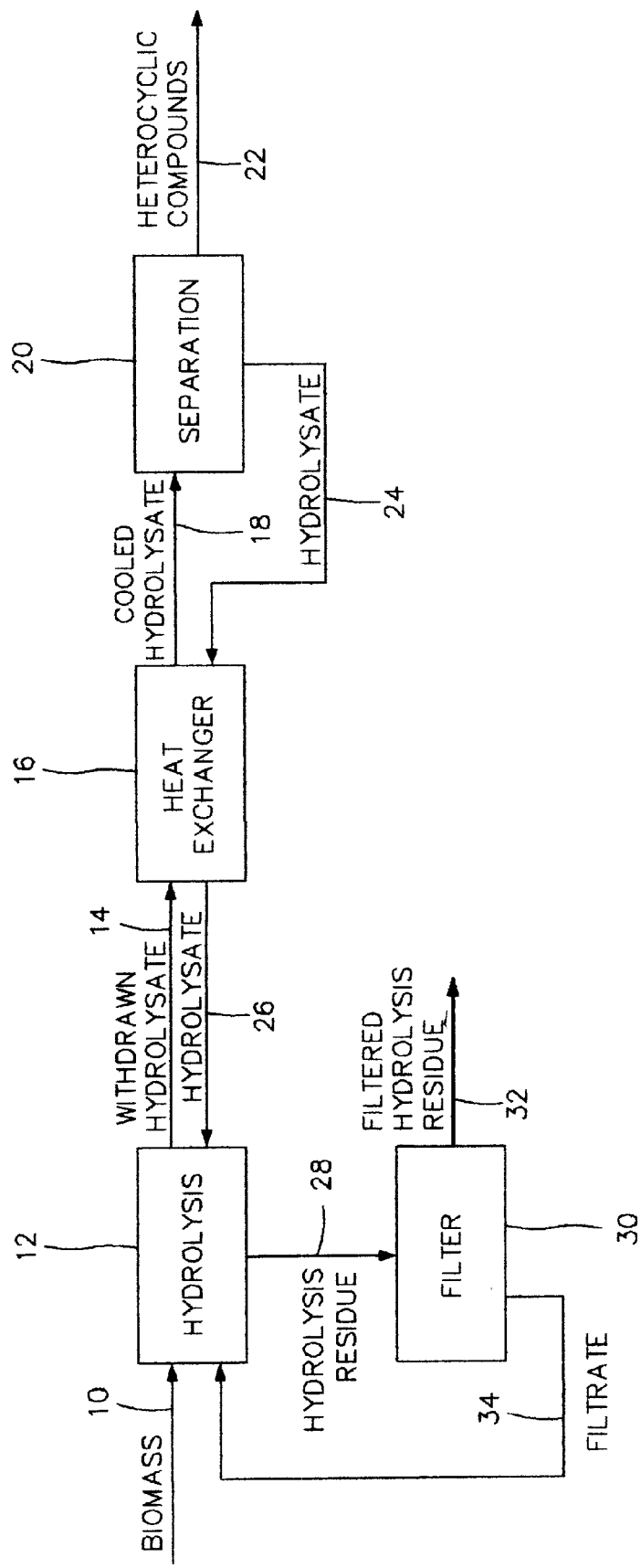
FIG. 1 is a flow sheet denoting the invention as set forth in the appended claims.

The flow diagram of FIG. 1 illustrates the general preferred embodiment of the present invention. In the diagram, rectangles represent stages, operations or functions of the present invention and not necessarily separate components. Details within each stage, operations or functions are not shown. Arrows indicate direction of flow of material in the method. Temperature control is maintained within the vessel from about 100° C. to about 250° C. to sustain hydrolysis. Acid for hydrolysis is sulfuric acid at a concentration ranging from of 1 to 10%.

Referring to FIG. 1, a method is depicted to form heterocyclic compounds by hydrolysis of a biomass. Biomass 10 is conveyed to hydrolysis stage 12 and subjected to hydrolysis, forming a hydrolysate 14, which is withdrawn from the hydrolysis stage 12 and conveyed to heat exchanger stage 16 wherein heat is exchanged from hydrolysate 24 to convey heated hydrolysate 26 to the hydrolysis stage 12. Cooled hydrolysate 18 is forwarded to separation stage 20 to separate heterocyclic compounds 22 from cooled hydrolysate 18 to be forwarded to heat exchange stage 16. Details of the separation stage 20 are extraneous to the function and are therefore omitted from FIG. 1. Cooled heat exchanged hydrolysate 18 is subject to additional treatment within FIG. 3 and FIG. 4. Hydrolysis residue 28 from hydrolysis stage 12 is conveyed to filter stage 30 and subjected to filtration to produce filtrate 34 and filtered hydrolysis residue 32. Filtrate 34 is recycled and conveyed to hydrolysis stage 12. Filtered hydrolysis residue 32 is subject to additional treatment within FIG. 2. Hydrolysis residue 32 will typically contain lignins The disclosed method is customarily accomplished in a continuous fashion.

Figure 2:
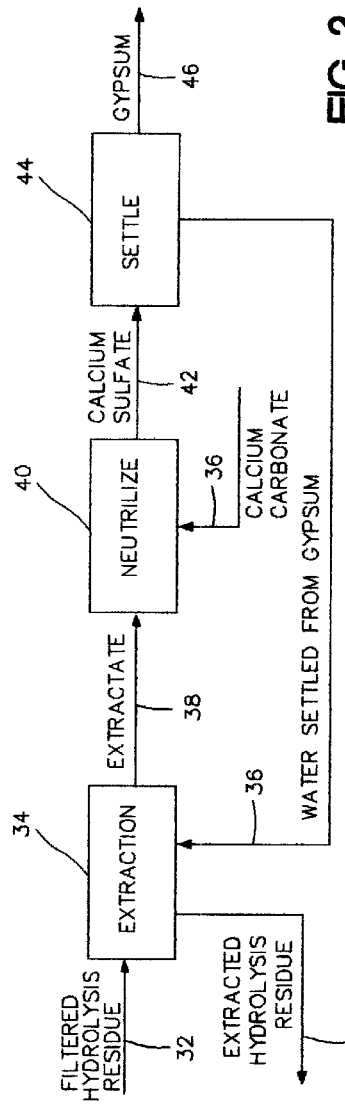
FIG. 2 is a flow sheet denoting a method to extract acid from hydrolysis residue.

Referring to FIG. 2, filtered hydrolysis residue 32 is conveyed to extraction stage 34 and extracted to produce an extractate 38 and extracted hydrolysis residue 32A. Extractate 38 conveyed to neutralize stage 40 is neutralized by addition of calcium carbonate 36 to create a solution containing calcium sulfate 42 and is conveyed to settle stage 44 to settle and produce gypsum 46 and water 36, settled from gypsum, for recycle to extraction stage 34. Gypsum 46, upon settling, is removed from the settle stage 44 and is discarded. Water 36, settled from gypsum, contains dissolved calcium sulfate and is conveyed to extraction stage 34. Extracted hydrolysis residue 32A, is substantially devoid of acid but contains a trace of dissolved calcium sulfate. The filtered solids containing acid are substantiality neutralized by chemicals selected from the group consisting of inorganic bases and inorganic salts including an individual or a combination thereof.

Figure 3:
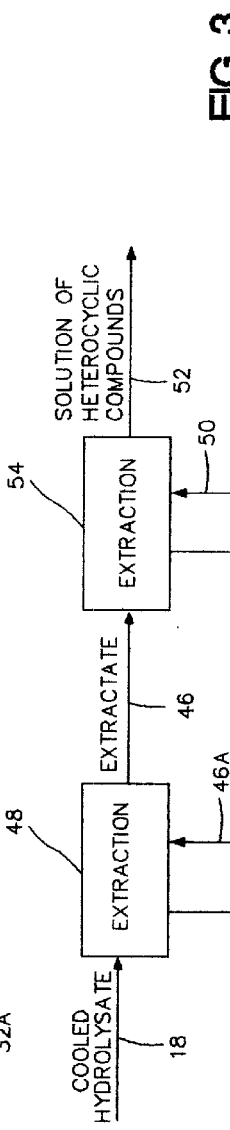
FIG. 3 is a flow sheet denoting a method to produce heterocyclic compounds from a cooled hydrolysate by extraction.

Referring to FIG. 3, cooled hydrolysate 18 is conveyed to extraction stage 48 and is extracted by a solvent 46A, insoluble in water but soluble in heterocyclic compounds, to produce extractate 46 and extracted hydrolysate 24 to be recycled to heat exchanger stage 16. The solvent 46A is often an organic halide. Extractate 46 is conveyed to extraction stage 54 to be extracted by water 50 to form a solution of heterocyclic compounds 52. Extracted solvent 46A, insoluble in water but soluble in heterocyclic compounds, is recycled to extraction stage 48. The solution of heterocyclic compounds 52 likely contains a solvent which is then separated from the solution of heterocyclic compounds by distillation.

Figure 4:
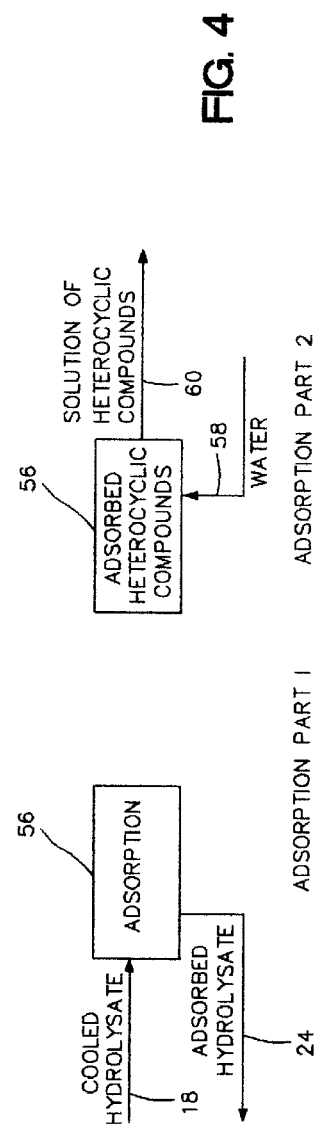
FIG. 4 is a flow sheet denoting a method to produce heterocyclic compounds from a cooled hydrolysate by adsorption.

Referring to FIG. 4, cooled hydrolysate 18 is conveyed to adsorption stage 56 and is adsorbed to produce an adsorbate, substantially devoid of heterocyclic compounds, of adsorbed hydrolysate 24 to be recycled to heat exchanger stage 16 to conclude adsorption part 1. In batch fashion, adsorption part 2 employs the same adsorption stage 56 to become adsorbed heterocyclic compounds stage 56. Adsorbed heterocyclic compounds stage 56, treated by water 58, frees heterocyclic compounds form the adsorbed heterocyclic compounds stage 56 to form a solution of heterocyclic compounds 60. The desorbed adsorbent required in adsorption stage 56 is reactivated to continue adsorption within adsorption stage 56. The adsorbent, capable of adsorbing heterocyclic compounds, is selected from the group consisting of activated charcoal, fullers earth and alumina including an individual or a combination thereof Accordingly the adsorption and desorption operations are accomplished batch ways.

What is claimed is:

1. A method to produce sugars from a biomass by hydrolysis and subject the sugars to dehydration to form heterocyclic compounds which comprises:

providing a vessel for said hydrolysis with an acid, and providing a biomass to said vessel, and subjecting said biomass, within said vessel, to said hydrolysis and reaction within said acid to form a hydrolysate, containing said heterocyclic compounds and said acid, and withdrawing said hydrolysate from said vessel, and separating means for removing said heterocyclic compounds from said hydrolysate to provide a hydrolysate substantially devoid of heterocyclic compounds for recycle to said vessel and heterocyclic compounds for subsequent processing, and withdrawing solids, remaining from said hydrolysis of said biomass, from said vessel, and filtering said solids resulting in a filtrate for recycle to said vessel and filtered solids, for subsequent processing, thereby removing heterocyclic compounds, derived from a biomass, from said vessel and removing solids remaining from hydrolysis of biomass from said vessel.

2. The method of claim 1 wherein said separating means is extraction by a solvent capable of dissolving said heterocyclic compounds forming an extractate of a hydrolysate substantially devoid of heterocyclic compounds for recycle to said vessel.

3. The method of claim 2 wherein said solvent capable of dissolving said heterocyclic compounds and insoluble in aqueous solutions is selected from the group consisting of organic solvents and cyclic compounds including an individual or a combination thereof.

4. The method of claim 2 wherein said solvent capable of dissolving the heterocyclic compounds is an organic halide.

5. The method of claim 1 wherein said filtered solids containing acid are substantiality neutralized by chemicals selected from the group consisting of inorganic bases and inorganic salts including an individual or a combination thereof.

6. The method of claim 1 wherein said filtered solids containing acid are substantiality neutralized by addition of calcium carbonate.

7. The method of claim 1 wherein said heterocyclic compounds include hydroxymethylfurfural and furfural.

8. The method of claim 1 wherein said heterocyclic compounds are derived from hemicellulose contained in said biomass.

9. The method of claim 1 wherein said biomass forms hydroxymethylfurfural from cellulose contained within said biomass.

10. The method of claim 1 wherein said acid for said hydrolysis is selected from the group consisting of inorganic acids and organic acids including an individual or a combination thereof.

11. The method of claim 1 wherein said acid for said hydrolysis is sulfuric acid.

12. The method of claim 1 wherein said acid for said hydrolysis is sulfuric acid at a concentration ranging from of 1 to 10%.

13. The method of claim 1 wherein said solids remaining from said hydrolysis contain lignins derived from a biomass.

14. The method of claim 1 wherein said separating means is an adsorbent capable of adsorbing said heterocyclic compounds forming a hydrolysate substantially devoid of heterocyclic compounds for recycle to said vessel and adsorbed heterocyclic compounds.

15. The method of claim 14 wherein said adsorbed heterocyclic compounds is desorbed by water forming a solution of heterocyclic compounds and adsorbent.

16. The method of claim 14 wherein said adsorbent is selected from the group consisting of activated charcoal, fullers earth and alumina including an individual or a combination thereof.

17. The method of claim 1 wherein said hydrolysis is subjected to temperature control to sustain hydrolysis.

18. The method of claim 1 wherein said biomass is selected from the group consisting of wood, waste paper and municipal solid waste including an individual or a combination thereof.

19. The method of claim 1 wherein said heterocyclic compounds are liquid fuels derived from a biomass.

20. The method of claim 1 wherein said method is accomplished in a continuous fashion.

* * * * *